United States Patent [19]

Herdeis et al.

[11] Patent Number: 5,889,183
[45] Date of Patent: Mar. 30, 1999

[54] β-AMINOETHANESULPHONYLAZIDE THEIR USE FOR THE PREPARATION OF 2-AMINOETHANE-SULPHONAMIDE (TAURYLAMIDE), TAUROLIDINE OR TAURULTAM AND THEIR ACID ADDITION SALTS

[76] Inventors: Claus Herdeis, Strassbergerstr. 18, D-80809, München; Christian Edwin Weis, Jägerstrasse 5 a, D-97297, Waldbuttelbrunn, both of Germany

[21] Appl. No.: 910,744

[22] Filed: Aug. 13, 1997

[30] Foreign Application Priority Data

Mar. 4, 1997 [DE] Germany .................. 197 08 782.5

[51] Int. Cl.[6] ............. C07C 143/76; C07D 285/16; A61K 31/54
[52] U.S. Cl. ............... 544/8; 514/222.5; 552/5; 544/8
[58] Field of Search ............... 552/5; 544/148; 514/222.5

[56] References Cited

U.S. PATENT DOCUMENTS

| 2,184,279 | 12/1939 | Christiansen | 260/556 |
| 4,604,391 | 8/1986 | Pfirrmann | 514/222 |
| 5,077,281 | 12/1991 | Reinmuller | 514/56 |
| 5,417,975 | 5/1995 | Lussi et al. | 424/423 |

FOREIGN PATENT DOCUMENTS 19515976 10/1996 Germany .

OTHER PUBLICATIONS

Koller, et al: "Synthesis and Properties of B–Sultams", Tetrahedron Letters, vol. 24, No. 21, pp. 2131–2134.

*Primary Examiner*—Jose'G. Dees
*Assistant Examiner*—Sabiha N. Qazi
*Attorney, Agent, or Firm*—Pillsbury Madison & Sutro LLP

[57] ABSTRACT

A novel process for the preparation of taurylamide or its acid addition salts and the compounds taurolidine or taurultam obtainable therefrom, in which cysteamine or cystamine, in particular in the form of acid addition salts, is used as a starting material and in which the key intermediate is the compound β-aminoethanesulphonylazide, in particular in the form of a water-soluble acid addition salt.

16 Claims, No Drawings

β-AMINOETHANESULPHONYLAZIDE THEIR USE FOR THE PREPARATION OF 2-AMINOETHANE-SULPHONAMIDE (TAURYLAMIDE), TAUROLIDINE OR TAURULTAM AND THEIR ACID ADDITION SALTS

The present invention relates to the novel compound β-aminoethanesulphonylazide (2-aminoethanesulphonic acid azide) and its salts with acids, in particular its hydrohalides, processes for their preparation and their use according to the Patent Claims.

β-Aminoethanesulphonylazide, in particular in the form of its salts with acids and in turn preferably in the form of its hydrochloride, is a novel intermediate for the preparation of taurylamide or of taurolidine or taurultam which can be prepared therefrom in a manner known per se. By the provision of β-aminoethanesulphonylazide and its subsequent smooth conversion by catalytic hydrogenation into taurylamide, it is possible to provide an improved process for the preparation of taurylamide or of taurolidine or taurultam.

The novel process, which takes place via the intermediate β-aminoethanesulphonylazide or a salt thereof, also permits the preparation of taurylamide or of taurolidine or taurultam starting from a starting material other than that usually used to date, namely from 2-aminoethanethiol (cysteamine) which is commercially available at relatively favourable costs. Instead of cysteamine, the corresponding disulphide (cystamine; bis(2-aminoethyl) disulphide), which is likewise available as a commercial product, may also be used as a starting material. Both starting materials, cysteamine and cystamine, are used in particular in the form of their salts with inorganic acids, in particular of the hydrochlorides.

Taurolidine and taurultam are compounds of the formulae:

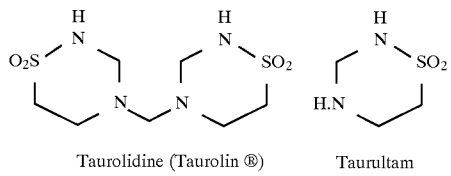

Taurolidine (Taurolin®)    Taurultam

Taurolidine is an antibacterial and antiendotoxic substance which is used in particular in the form of an antiseptic wash solution in surgery for washing out the abdominal cavity and, compared with other antiseptic substances, has the advantage that it also renders released toxins harmless and can thus help to prevent a septic shock. Taurolidine is commercially available in the form of solutions for hospital use (Tauroline® solution from Geistlich Söhne AG, Wolhusen, Switzerland).

A further possible use for taurolidine is described in Patent Application DE 4239206 A1, which relates in particular to the use in hair shampoos, where it serves for improving the shapability of the hair.

Taurultam can be obtained by hydrogenation of taurolidine and has similar properties to the latter and can therefore replace it in many applications.

The known preparation of taurolidine takes place via the compound taurylamide or its salts with acids as an important intermediate. Taurylamide is reacted with 1.5 equivalents of formaldehyde in the final step in the known preparation of taurolidine under basic conditions. This preparation is described in Swiss Patent 482 713, in particular in Example 4. A further description appears, for example, in Hagers Handbuch der Pharmazeutischen Praxis, 5th Edition, Vol. 9, pages 779–780, and in the monograph by Brückner, W. L.; Pfirrmann, R. W., Taurolin (1985), Verlag Urban and Schwarzenberg, Munich, Vienna, Baltimore. In the processes to date for the preparation of the required taurylamide or its acid addition salts, β-aminoethanesulphonic acid (taurine) is used as a starting material. The known processes (cf. DE-A-3 620 667 or U.S. Pat. No. 2,184,279) for the preparation of taurylamide, starting from taurine, are multistage processes which require a relatively large amount of chemicals and simultaneously produce considerable amounts of undesired byproducts which have to be disposed of. In such processes, the amino group of the taurine must first be protected (for example by reaction with phthalic anhydride or trifluoroacetyl chloride) so that the sulphonic group can then be converted with chlorinating agents (e.g. thionyl chloride, phosphoryl chloride) into a sulphonyl chloride group. The corresponding sulphonamide is then prepared by reacting the sulphonyl chloride, obtained after the chlorination, with ammonia, and the protective group for the β-amino group must then be eliminated again. The taurylamide is finally isolated in the form of its hydrochloride.

It is also known that taurylamide can be prepared starting from the unsaturated sulphonamide of the formula $CH_2=CHSO_2NH_2$ or from the corresponding unsaturated sulphonyl halide $CH_2=CHSO_2Hal$ (Hal=halogen, in particular Cl).

Processes which start from vinylsulphonamides have the disadvantage that undesired byproducts form and the vinylsulphonic acid derivatives are relatively unstable compounds, making the process more difficult to carry out. Moreover, vinylsulphonic acid derivatives are relatively expensive starting substances, the costs of which affect the end product.

In view of the required reagents and the byproducts of the process, the processes described at the outset and starting from taurine are disadvantageous from the point of view of environmental compatibility and, as multistage processes, are complicated and also unsatisfactory with regard to the total yield. Thus, in the five stage process for the preparation of taurylamide currently used in practice, the amount of undesired byproducts corresponds approximately to the amount of taurylamide prepared.

German Patent DE 195 15 976 C1 has disclosed a process in which taurylamide or taurolidine is prepared by a fundamentally different method, in which a diazide, β-azidoethanesulphonylazide, is prepared starting from in particular β-chloroethanesulphonyl chloride, by reaction with a suitable azide, and can be converted by catalytic hydrogenation into taurylamide, which in turn can then be further processed to taurolidine in a manner known per se.

Compared with the conventional processes, the process according to DE 195 15 976 C1 has the advantage that the preparation of taurolidine takes place without formation of significant amounts of undesired byproducts and virtually quantitatively.

However, the potential tendency of β-azidoethanesulphonylazide to explode is a certain disadvantage of the process according to DE 195 15 976 C1. Furthermore, the stated process is still capable of improvement with regard to the costs of the starting compounds used and the solvent requirement.

It is therefore an object of the present invention to provide a novel compound which, while retaining important advantages of the azide compound according to DE 195 15 976 C1, is safer to handle and whose use as an intermediate permits the provision of a novel process for the preparation of taurylamide, which process has lower operating risks than the known processes and starts from more economically available starting compounds, so that overall an improved process for the preparation of taurolidine or taurultam is finally provided.

This object is achieved on the one hand by the novel compound β-aminoethanesulphonylazide and its salts with acids, in particular the hydrochloride.

The object is achieved on the other hand by providing a taurylamide synthesis or taurolidine or taurultam synthesis which takes place via the novel key compound β-aminoethanesulphonylazide, in particular in the form of its hydrochloride, as an intermediate.

A particular aspect of the present invention is that the preparation of taurolidine starting from a novel starting compound is provided, namely with the use of 2-aminoethanethiol (cysteamine) commercially available relatively economically or of the corresponding disulphide (cystamine) or of their salts with acids, in particular the hydrochlorides.

The novel process differs from the process according to DE 195 15 976 C1 essentially in that compounds which contain in the 2-position (β-position) an amino group capable of salt formation are used from the outset. The amino group can be protected during the reaction steps of the process by simple salt formation with an acid, in particular a strong monobasic mineral acid and preferably a hydrohalic acid, in particular with hydrogen chloride, and, owing to the solubility of the salt-like compound, permits the use of aqueous reaction media. Thus, the preparation of taurolidine can surprisingly also be carried out in the form of a "one vessel synthesis" in water as the reaction medium by the process according to the invention, as explained in more detail below.

According to the invention, β-aminoethanesulphonylazide is prepared in the form of a salt with an acid, in particular of the hydrochloride, by a process in which a compound of the formula (I)

where, in this compound, X and X' may be identical or different and are preferably each a halogen atom, in particular chlorine or bromine, occurs as an intermediate in the process stage preceding the introduction of the azide group. The stated compounds of the formula (I), which are salts of β-aminoethanesulphonyl halides, may also be referred to as salts of tauryl halides, for example, where both X and X' are chlorine, as tauryl chloride hydrochloride.

In these compounds of the formula (I), the halogen radical bonded to the $SO_2$ group can be replaced by nucleophilic substitution in a smooth reaction by an azide group, which can then be converted by catalytic hydrogenation, similarly to the process according to DE 195 15 976 C1, into an amide group.

It is in principle known that salts of β-aminoalkanesulphonyl halides with inorganic acids are obtainable by oxidative halogenation of β-aminoalkanethiols or β-aminoalkane disulphides (cf. for example Tetrahedron Letters, Vol. 24, No. 21, pages 2131–2134, 1983, and the literature cited therein; and Tetrahedron Letters, No. 3, pages 213–216, 1972). However, the conversion of such salts of 2-aminoalkanesulphonyl halides into taurylamide is not known. If an attempt is made, for example, to replace the halogen atom bonded to the sulphonyl group by an amino group by reaction with ammonia, the basicity of the ammonia results in the 2-amino group being liberated from its salt and the neutral compound reacting with cyclization to give the corresponding sultam compound (loc. cit.).

For example, by converting the β-aminoethanesulphonyl chloride hydrochloride into β-aminoethanesulphonylazide hydrochloride in a nucleophilic substitution reaction with the use of a suitable azide in a suitable polar solvent, the reaction leading to the sultam compound is avoided, and the taurylamide hydrochloride can then be prepared from the azide by simple catalytic hydrogenation.

In particular water, but if required also organic solvents, such as dipolar aprotic solvents, substituted and unsubstituted amides, cyclic and acyclic ethers and the like, may in principle be used as solvents for the reaction of the β-aminoethanesulphonyl chloride hydrochloride with a suitable azide. If water is used, quantitative conversion of β-aminoethanesulphonyl chloride hydrochloride into β-aminoethanesulphonylazide hydrochloride is achieved. At room temperature, the reaction is quantitatively complete after 15 minutes. Water is therefore the preferred reaction medium for the preparation, according to the invention, of β-aminoethanesulphonylazide or its acid addition salts. However, the use of other solvents having comparable dissolution behaviour, in particular solvents of high polarity, should not be ruled out.

When it is prepared by the process described below, the novel compound β-aminoethanesulphonylazide hydrochloride is a colourless crystalline compound (melting point: 155° C., recrystallized from absolute ethanol). It can be safely handled at room temperature but, like other sulphonylazides, has a tendency to decompose at higher temperatures (>200°). The compound is not sensitive to impact, which is a considerable advantage over 2-azidoethanesulphonylazide.

It has been found that β-aminoethanesulphonylazide or its acid addition salt can be reduced smoothly to the desired taurylamide or its acid addition salt. The reaction is preferably carried out as a catalytic hydrogenation in the presence of a metal catalyst (preferably palladium or platinum on a suitable carrier, such as active carbon) in a suitable solvent. The solvent is chosen with respect to its suitability as a hydrogenation solvent and moreover with respect to its easy and complete separation from the end product. Water or the lower alkanols $C_nH_{2n+1}OH$ have proved particularly suitable.

The taurylamide hydrochloride prepared by the hydrogenation of the azide can be isolated and can be converted into taurolidine in a known manner by the process of Swiss Patent 482 713 or as described in Example 2 under b) of DE 195 15 976 C1, with formaldehyde under basic conditions. Taurolidine can, if desired, also be converted into taurultam.

However, a particular advantage of the process according to the invention, also over the process according to DE 195 15 976, is that all reaction steps from the introduction of the azide group to the preparation of the end product taurolidine can be carried out in an aqueous medium without it being necessary to isolate the intermediates prepared.

Like the process according to DE 195 15 976 C1, the process according to the invention has the considerable advantage over the other processes of the prior art that sodium chloride is obtained as the only byproduct when the procedure is carried out using chlorides or hydrochlorides and $NaN_3$ as the azide. The catalyst can be regenerated, the procedure can be carried out in water and the reaction takes place virtually quantitatively.

A further important advantage of the process according to the invention is that the economically and commercially available compounds cysteamine and cysteamine hydrochloride (2-aminoethanethiol hydrochloride) or optionally cystamine or cystamine hydrochloride can be used as starting materials, with the result that the process according to the invention is advantageous compared with the process according to DE 195 15 976 C1 even in terms of costs.

The various aspects of the present invention are described in more detail below with reference to Examples.

EXAMPLE 1
Preparation of 2-aminoethanesulphonyl chloride hydrochloride (tauryl chloride hydrochloride) from cysteamine hydrochloride Cysteamine hydrochloride (5.74 g; 0.05 mol) was suspended in a mixture of tetrachloromethane/ethanol (50 ml/6 ml) in a three-necked flask with a mechanical stirrer, a gas inlet tube and an internal thermometer. The reaction mixture was cooled to about 5° C. with the use of external cooling with an ice/water mixture, after which chlorine gas was passed in while stirring and immediately reacted with the content of the reaction vessel. After chlorine gas had been passed in for about 15 minutes, the suspension assumed a creamy appearance and the reaction temperature increased to about 20° to 30° C. The gases formed during the reaction (HCl, ethyl chloride) were bound by being passed into an absorption liquid. The introduction of chlorine gas was continued until the reaction mixture had assumed a stable yellow colour (after about 45 min).

A colourless substance was suspended in the reaction mixture, and an investigation by $^1$H-NMR spectroscopy (in $D_2O$) showed that the starting compound had reacted quantitatively with a selectivity of more than 95%.

The tauryl chloride hydrochloride suspended in the reaction mixture was separated from the liquid reaction medium by means of a glass suction filter. Washing, for example with an organic solvent, is possible but is not essential. The product was dried in vacuo at room temperature and then further processed.

Tauryl chloride hydrochloride can be stored in a closed vessel without hydrolyzing. The compound is thermally stable.

When the batch size was increased starting from 1 mol (113.6 g) of cysteamine hydrochloride, tauryl chloride hydrochloride was obtained in quantitative yield.

Melting point (crude material) 155°–158° C.; IR (KBr): ν (cm$^{-1}$)=3300–2700, 2650, 2450, 2000–1900, 1600, 1550, 1515, 1460, 1450, 1410, 1400, 1380–1390, 1280, 1170, 1160, 1110, 1080, 1040, 950, 870, 840, 760, 700. $^1$H-NMR ($D_2O$, 200 MHz): δ (ppm)=3.71 (t, $^3$J=6.2 Hz, 2H), 4.41 (t, $^3$J=6.2 Hz, 2 H). $^{13}$C-NMR ($D_2O$, 50.3 MHz): δ=61.34 ($H_3N$—$CH_2$), 35.1 ($CH_2SO_2Cl$).

EXAMPLE 2
Preparation of β-aminoethanesulphonylazide hydrochloride (taurylazide hydrochloride) from β-aminoethanesulphonyl chloride hydrochloride (tauryl chloride hydrochloride)

Tauryl chloride hydrochloride and sodium azide were reacted with one another in a ratio of 1:1 in water. For this purpose, the calculated stoichiometric amount of sodium azide was dissolved in water and the solution was cooled to 5° C. Tauryl chloride hydrochloride was added while stirring and the reaction mixture was stirred for 15 min. By stripping off the water, a solid mixture of crystalline sodium chloride and taurylazide hydrochloride was obtained.

Melting point: 155° C. (from ethanol). IR (KBr): ν (Cm$^{-1}$)=3100, 2990, 2820–2920, 2120 (CN), 1590, 1560, 1500, 1450, 1390, 1360, 1340, 1230, 1200, 1180, 1120, 1100, 1040, 950, 870, 840, 745, 700. $^1$H-NMR ($D_2O$, 200 MHz): δ (ppm)=3.71 (t, $^3$J=6.4 Hz, 2H), 4.18 (t, $^3$J=6.4 Hz, 2H). $^{13}$C-NMR ($D_2O$, 50.3 MHz): δ (ppm)=52.61 ($H_3N$—$CH_2$), 34.63 ($CH_2SO_2N_3$).

EXAMPLE 3
Hydrogenation of β-aminoethanesulphonylazide hydrochloride to taurylamide hydrochloride The taurylazide hydrochloride product obtained according to Example 2 was dissolved in water, a hydrogenation catalyst (palladium on carbon) was added and the compound used was hydrogenated for 3 h while passing in hydrogen at a pressure of 40 bar. By monitoring the hydrogenation, it was found that the hydrogenation was completed quantitatively after 3 h ($^1$H-NMR and $^{13}$C-NMR control spectra showed only product signals). The catalyst was then filtered off from the reaction mixture, and the reaction medium, water, was removed in vacuo. Absolute ethanol was added to the tacky colourless residue obtained, and the latter was partially dissolved in the ethanol by heating. The product was completely crystallized from the solution on cooling and was separated from the liquid phase by filtration. The filtration residue obtained consisted of taurylamide hydrochloride and sodium chloride. Taurylamide hydrochloride was obtained in pure recrystallized form with the use of absolute ethanol.

A peculiarity of the purification by recrystallization is that recrystallization with the use of ethanol denatured by added petroleum ether is not possible. Yield: 60–70% (after recrystallization from absolute ethanol)

Melting point: 132°–134° C. (from absolute ethanol); Melting point data of various producers: Geistlich: 130°–132° C. (recrystallized); Kali-Chemie: 132° C. On further heating, a brown discoloration occurs at 248°–252° C. and the product decomposes. IR: ν (cm$^{-1}$) 3220, 3100–3200 (br), 2920, 2710, 1950, 1600, 1585, 1560, 1490, 1455, 1415, 1390, 1320, 1290, 1150, 1090, 1030, 940, 915, 880, 840, 750. $^1$H-NMR ($D_2O$, 200 MHz): δ (ppm)=3.56 (t, $^3$J=6.4 Hz, 2H), 3.74 (t, $^3$J=6.4 Hz, 2H). $^{13}$C-NMR ($D_2O$, 50.3 MHz): δ (ppm)=51.76 ($H_3N$—$CH_2$), 35.07 ($CH_2SO_2N_3$).

EXAMPLE 4
Preparation of taurolidine from tauryl chloride hydrochloride without isolation of the intermediates As described in Example 2, the calculated stoichiometric amount of sodium azide was dissolved in water and the solution was cooled to 5° C. Thereafter, a corresponding stoichiometric amount of tauryl chloride hydrochloride was added while stirring, and stirring was continued until complete dissolution had been achieved (after about 15 min). The hydrogenation catalyst (palladium on carbon) was added directly to the solution obtained and, as described in Example 3, hydrogenation was carried out for 3 h at 40 bar by passing in hydrogen. After the end of the 3-hour hydrogenation ($^1$H-NMR and $^{13}$C-NMR control spectra showed only product signals), the hydrogenation catalyst was filtered off from the reaction mixture. The taurylamide hydrochloride solution obtained as filtrate was brought to the concentration stated in the literature (loc. cit.) by stripping off a part of the water and was cooled to 5° C., and the amounts of sodium hydroxide solution (30%) and formaldehyde solution (37%) required for the conversion of the taurylamide to taurolidine by the known processes were added. With continuing stirring, taurolidine is precipitated after some time as a colourless, finely crystalline powder, which was separated from the liquid reaction mixture by filtration under suction over a glass frit. Drying was carried out under a refined vacuum, after which the melting point of the product was 172°–175° C.

A yield of 90%, based on the tauryl chloride hydrochloride used, was calculated.

We claim:

1. A compound selected from the group consisting of β-aminoethanesulphonylazide and its salts with acids.

2. Process for the preparation of a β-aminoethanesulphonylazide salt, wherein
   (i) 2-aminoethanethiol or bis(2-aminoethyl) disulphide in the form of one of their salts with an acid is converted, by oxidative halogenation, into a 2-aminoethanesulphonyl halide salt
   (ii) and the β-aminoethanesulphonyl halide salt obtained is converted into salt of 2-aminoethanesulphonylazide by reaction with a nucleophilic azide.

3. Process according to claim 2, wherein, in stage (i), 2-aminoethanethiol or bis(2-aminoethyl) disulphide in the form of their hydrochlorides is converted by reaction with gaseous chlorine in the presence of ethanol, into 2-aminoethanesulphonyl chloride hydrochloride.

4. Process according to claim 2, wherein stage (ii) is carried out in a polar solvent as the reaction medium.

5. Process according to claim 2, wherein the azide used is an alkali metal azide.

6. Process according to claim 2, wherein the salts are acid addition salts of a hydrohalic acid.

7. A process for preparing a compound selected from the group consisting of 2-aminoethanesulphonamide hydrochloride taurolidine and taurultam wherein
   (i) 2-aminoethanethiol or bis(2-aminoethyl) disulphide in the form of one of their salts with an acid is converted, by oxidative halogenation, into a 2-aminoethanesulphonyl halide salt;
   (ii) the 2-aminoethanesulphonyl halide salt obtained is converted into a salt of 2-aminoethanesulphonylazide by reaction with a nucleophilic azide; and
   (iii) said 2-aminoethanesulphonylazide salt is converted to said compound selected from the group consisting of 2-aminoethanesulphonamide hydrochloride taurolidine and taurultam.

8. Method according to claim 7, wherein β-aminoethanesulphonylazide hydrochloride is converted into 2-aminoethanesulphonamide hydrochloride by catalytic hydrogenation.

9. Method according to claim 8, wherein the catalytic hydrogenation is carried out in an aqueous medium and, after the hydrogenation catalyst used has been separated off, the product solution which contains the 2-aminoethanesulphonamide hydrochloride formed is further processed directly to taurolidine by addition of formaldehyde and of a base.

10. A method for preparing a compound selected from the group consisting of taurolidine and taurultam which comprises converting 2-aminoethanethiol or bis(2-aminoethyl) disulphide into said compound.

11. Process according to claim 4 wherein the polar solvent is water or $C_1$–$C_4$-alkanol.

12. Process according to claim 5 wherein the alkali metal azide is sodium azide.

13. Process according to claim 6 wherein the salt is a hydrochloride.

14. The method which comprises preparing 2-aminoethanesulphonamide hydrochloride by catalytic hydrogenation of β-aminoethanesulphonylazide hydrochloride.

15. A method according to claim 14 wherein the 2-aminoethanesulphonamide hydrochloride is converted to taurolidine or taurultam.

16. The product obtained according to the method of claims 14 or 15.

* * * * *